United States Patent
Meissner

(10) Patent No.: US 12,251,480 B2
(45) Date of Patent: Mar. 18, 2025

(54) COLLIMATED ELECTRON BEAM STERILIZATION DOSE

(71) Applicant: ABBOTT DIABETES CARE INC., Alameda, CA (US)

(72) Inventor: Jörn Meissner, Neubiberg (DE)

(73) Assignee: ABBOTT DIABETES CARE INC., Alameda, CA (US)

( * ) Notice: Subject to any disclaimer, the term of this patent is extended or adjusted under 35 U.S.C. 154(b) by 750 days.

(21) Appl. No.: 17/292,038

(22) PCT Filed: Oct. 21, 2019

(86) PCT No.: PCT/EP2019/078607
§ 371 (c)(1),
(2) Date: May 7, 2021

(87) PCT Pub. No.: WO2020/094379
PCT Pub. Date: May 14, 2020

(65) Prior Publication Data
US 2021/0393816 A1 Dec. 23, 2021

(30) Foreign Application Priority Data
Nov. 9, 2018 (EP) .................................... 18205536

(51) Int. Cl.
*A61L 2/00* (2006.01)
*A61L 2/08* (2006.01)
(Continued)

(52) U.S. Cl.
CPC ................ *A61L 2/087* (2013.01); *G21K 1/02* (2013.01); *G21K 5/04* (2013.01); *A61L 2202/24* (2013.01)

(58) Field of Classification Search
CPC .......... A61L 2/087; A61L 2/0047; A61L 2/08; A61L 2202/24; G21K 5/04
(Continued)

(56) References Cited

U.S. PATENT DOCUMENTS 3,227,880 A * 1/1966 Wideroe .................. G21K 1/02
976/DIG. 428
4,220,866 A 9/1980 Taumann
(Continued)

FOREIGN PATENT DOCUMENTS

WO WO-2017219291 A1 * 12/2017 ............... A61N 5/02

OTHER PUBLICATIONS

International Search Report dated Jan. 2, 2020 for corresponding International Application No. PCT/EP2019/078607.

*Primary Examiner* — Monzer R Chorbaji
(74) *Attorney, Agent, or Firm* — Baker Botts L.L.P.

(57) ABSTRACT

A collimator to control and/or focus radiation originating from an electron beam source, comprising at least a first absorber comprising a first side configured to allow the beam entry and a second side opposite to the first side; and at least one recess in the first absorber wherein a first contour of the recess at the first side is larger than a second contour of the recess at the second side. Further, a to control and/or focus radiation originating from an electron beam source, comprising the steps of providing at least a first collimator according to any of the preceding collimator claims; providing a product to be sterilized; arranging or assembling the collimator with the respect to the product so that the collimated electrons are oriented towards at least one part of the product to be sterilized and electrons are absorbed towards at least another part of the product that to be not harmed by those electrons.

17 Claims, 5 Drawing Sheets

(51) Int. Cl.
*A61N 5/00* (2006.01)
*G01N 21/00* (2006.01)
*G01N 23/00* (2006.01)
*G21K 1/02* (2006.01)
*G21K 5/04* (2006.01)

(58) Field of Classification Search
USPC ...... 422/22, 24; 250/453.11, 454.11, 455.11, 250/492.1
See application file for complete search history.

(56) References Cited

U.S. PATENT DOCUMENTS

| | | |
|---|---|---|
| 5,160,847 A | 11/1992 | Leavitt |
| 5,267,294 A | 11/1993 | Katsuhiro |
| 6,594,156 B1 | 7/2003 | Van Antwerp |
| 2017/0154751 A1* | 6/2017 | Brown .................. H01J 37/141 |

* cited by examiner

COLLIMATED ELECTRON BEAM STERILIZATION DOSE

RELATED APPLICATIONS

The present application is a U.S. National Stage application under 35 USC 371 of PCT Application Serial No. PCT/EP2019/078607, filed on 21 Oct. 2019; which claims priority from EP Patent Application 18205536.8, filed 9 Nov. 2018, the entirety of both of which are incorporated herein by reference.

FIELD

This invention is directed to the collimation of electron beam radiation in industrial application, such as sterilization of goods. Collimation, in general, is a focusing of radiation dose by guidance of the scattering pathways of electrons.

BACKGROUND

Many medical devices are sterilized by using electron beam irradiation. The radiation dose is typically applied over the complete device. All devices contain parts that must receive a minimum radiation dose. Some devices contain radiation sensitive parts, for instance electronic devices, semiconductors, or pharmaceuticals. Typically, the minimum sterilization dose is much higher than the maximum tolerable dose by the radiation sensitive parts. Separating these parts from the medical device during radiation sterilization may not be desirable for economic or other reasons.

An electron beam is emitted from an electron source, such as an electron accelerator, and distributed over the device to be sterilized. This is typically done by a magnetic scanning system that deflects the electron beam on one or two direction(s) to achieve an illumination of the surface of the device or of many devices sterilized in a batch. The electron beam has a defined angular range of incidence on the devices to be sterilized. In many cases this would be normal or near normal to the devices' surface, but this is not required.

A number of prior art is known, such as U.S. Pat. No. 5,160,847 (A), a dynamic multivane electron arc beam collimator having collimation vanes, means for controlling the vanes, and local controllers at the collimation site which dynamically define an electron aperture which defines the electron field of an electron beam emitted by a linear accelerator during electron arc therapy. The collimator can be attached to or detached from the head of a linear accelerator. The collimator provides for improvement in electron arc therapy dose uniformity.

Further, U.S. Pat. No. 4,220,866 (A) discloses an electron collimator that is to be mounted on the accessory holder of an electron accelerator. In radiation therapy, the down beam end of the applicator is to contact the patient to establish a precise spacing of the electron source therefrom. The legs of the L-shaped collimator plates have rods secured to the corner part thereof which link pairs of overlapping legs to a common carrier for joint lateral adjustment toward and away from the beam axis. The rods slide in apertures in the carrier as the legs are adjusted longitudinally. Cornered wall elements are secured to each collimator plate and overlap each other to surround the beam path, and have in-turned closely overlapping edges which terminate flush with the inner margins of the collimator plates so as to provide further electron collimation and to provide an essentially smooth patient contacting end face.

A huge number of scientific publications are known to the person skilled in the art.

SUMMARY

The goal underlying the present invention is to provide an improved or ameliorated system of a collimator with at least one absorber. The goal can be reached by the subject matter of the present invention and as further exemplified by the description and the claims.

The subject matter in accordance with the claims and/or the description attains this goal.

This invention preferably provides for a method and system to collimate electron beam radiation or at least to minimize radiation dose efficiently so that radiation damage to radiation sensitive parts in the immediate vicinity of high radiation dose areas is reduced or reduced to acceptable levels.

The present invention is directed to collimate, control and/or focus radiation originating from an electron beam source. It can comprise at least a first absorber comprising a first side configured to allow the beam entry and a second side essentially opposite to the first side or being directed towards a product. Materials reduce at least the kinetic energy of electrons by scattering and absorption processes. Given enough material electrons are stopped. There can be at least one recess in the first absorber that can form the basis for the collimator. The recess can extend through the absorber in the general direction of the electon beam(s). A first contour of the recess at the first side can be larger than a second contour of the recess at the second side.

The invention can alternatively also be called an electron absorber with a collimator. In this case there is an absorber to control and/or focus radiation originating from an electron beam source, comprising at least a first side configured to allow the beam entry and a second side opposite to the second side; and at least one collimator with at least one recess in the first absorber wherein a first contour of the recess at the first side is larger than a second contour of the recess at the second side.

The recess can comprise at least one of a truncated conical shape or a truncated pyramid shape. Other or additional shapes can also be realized according to the needs. The size of the first contour can be larger than the size of the second contour. The entry surface can be larger than the exit surface of the recess.

According to an embodiment the first contour can be a circle or closed to a circle defining the first recess opening at the first side and having a diameter of $D_1$ and the second contour can be a circle or closed to a circle defining the second recess opening at the second side and having a diameter $d_1$. Other shapes for both contours can be also used according to the needs.

The size of the first and the second contour can be configured so that the dose ratios $P_0/P_e$ are optimized at constant or nearly or essentially constant L, whereby $D_1$ and $d_1$ are configured to optimize electronic dose contributions to $P_0$ and $P_1$, wherein $P_0$ being the dose ratio at the second side, $P_e$ the dose ratio at the first side and $P_1$ being the dose ratio at a given at a position behind the second side.

The ratio $D_1/d_1$ can be at least 1.25, preferably 1.5, more preferably 2, and even more preferably 2.5. Alternatively or additionally, the ratio $D_1/d_1$ can be at most 5, preferably 4, even more preferably 3.33, and even more preferably 3.

$D_1$ can range from 3 mm to 20 mm, preferably from 5 to 15 mm, more preferably from 7.5 mm to 12.5 mm, more preferably from 9 mm to 11 mm, and most preferably 10 mm. Alternatively or additionally $d_1$ can be from 1 mm to 10 mm, preferably from 2 to 8 mm, more preferably from 1 mm to 6 mm, more preferably from 2 mm to 5 mm, and most preferably from 3 to 4 mm. These values can be particularly advantageous for certain applications, such as the sterilization of devices were sensors that are intended for subcutaneous use (sterile) and electronic devices (radiation sensitive) are installed in the proximity on the same device. In this case the collimator can be attached to or even integrated into an applicator for the device to facilitate the electron beam sterilization process in its final packaging or reduce transportation volume and cost.

The first absorber can have more than one layer that are preferably made of different materials. The layers then can have different properties with respect to the electron interaction and can be laminiated one on the other or can even have distance or gaps to each other.

The recess can comprise at least one of a truncated conical shape or a truncated pyramid shape in each layer with convergent inclination towards the second side. That means that the angles of inclination of the side walls get smaller and smaller. If needed, the opposite arrangement or a combinded arrangement can be also made use of, i.e. that the angles of inclination get larger and larger or larger and smaller and vice versa.

The first absorber can comprise at least one of a polymer, an electrically conducting polymer, a polymer comprising metal particles, a polymer comprising at least one metal piece, a metal, a ceramic, wood and/or cardboard. It can also have any combination of these materials or can comprise other materials or combinations thereof.

Additionally, at least a second absorber can be provided behind or downstream with respect to the second side of the collimator and/or absorber. Any absorber can cause the electrons to generate X-rays and can have an impact of the ratio $P_0/P_1$ on them.

The second absorber can be attached to and/or integrated into the first absorber and has preferably an annullar shape. It can also have any modified or other shape depending on the needs.

The second absorber can be separate from the first absorber and can be configured to protect and/or encapsulate an element, such as an integrated circuit of a product to be sterilized.

The at least second absorber comprises a material with a higher average atomic number than the first absorber. It can further comprises at least one of a polymer, an electrically conducting polymer, a polymer comprising metal particles, a polymer comprising at least one metal piece, a semiconductor and/or a metal, preferably stainless steel or aluminum, tantalum, tungsten, lead.

The first absorber can comprise at least 2 layers, as mentioned, with the thickness of the first layer $L_1$ is selected based on the range of electrons beams at the selected electron beam energy in the same material without recess, and wherein the thickness of the successive layers $L_2+ \ldots +L_n$ can be optimized or configured for the absorption of scattered electrons and x-rays generated by the electron interaction with all materials.

The first and/or second absorber(s) is/are configured so that the dose ratios $P_0/P_e$ and/or $P_0/P_1$ can be simultaneously configured at a constant L, whereby $D_1$ and $d_1$ can be optimized or configured to enhance or optimize electronic dose contributions to $P_0$ and $P_1$ wherein $P_e$ is the dose at the first side of the first absorber and $P_0$ is the dose at the second side of the absorber in the region of the recess and $P_1$ is the dose at the second side of the absorber away from the region of the recess.

The first and/or second absorber(s) can have more than one layer and at each layer the diameter at the more open side is $D_x$ and at the more closed side is $d_x$ and the ratio(s) of $D_x/d_x$ are configured to optimize or enhance remaining electron scatter and x-ray dose contributions to $P_0$ and $P_1$.

The present invention also relates to an assembly of the collimator as described above and/or below and a product to be sterilized. Then the collimator and the product can be attached and/or assembled to each other.

The present invention also relates to a respective method to control and/or focus radiation originating from an electron beam source. Any of the above features can be also made use of in respective method steps that are in any combination also part of the present invention. The present invention can comprise the steps of providing at least a first collimator according to any of the preceding collimator claims and providing a product to be sterilized. Both can be constantly arranged together with each other or just assembled for the use of the sterilization process. The invention can also embrace the step of arranging or assembling the collimator with the respect to the product so that the collimated electrons are oriented towards at least one part of the product to be sterilized and electrons are absorbed towards at least another part of the product that to be not harmed by those electrons.

A further step in accordance with the present invention can comprise the step of irradiating the product with electrons from the electron beam source.

Moreover, there can be provided the further step(s) of conveying the product continuously while simultaneously irradiating it from top and/or from bottom and/or from one or both sides.

The present invention is further directed to the use of any of the above and/or below mentioned collimators and/or methods for the sterilization of at least pre-defined parts of medical products.

The use is particularly suitable and can be advantageous for the sterilization of at least pre-defined parts of medical devices that will be used sub-cutane in a patient and/or of at least one of pacemakers, automatic drug delivery components, blood value(s) measuring/monitoring components, cardiac devices, such as stents and cathethers, immunotherapy components.

The present invention has the preferred advantage that the electron dose gradient can be steeply formed according to the needs for the sterilization of the respective product. Thus, parts of the product that need to be sterilized can be sterilized securely and other more sensitive parts of the product can be protected from the electrons and X-rays.

The present invention can thus be easily assembled into a product to be sterilized easily thereafter. It can also be just for the sterilization be attached to the product like a mask. This enhances the safety and also a more efficient use of the irradiation and the energy consuming generation of the electrons.

EMBODIMENTS

Figure 1:
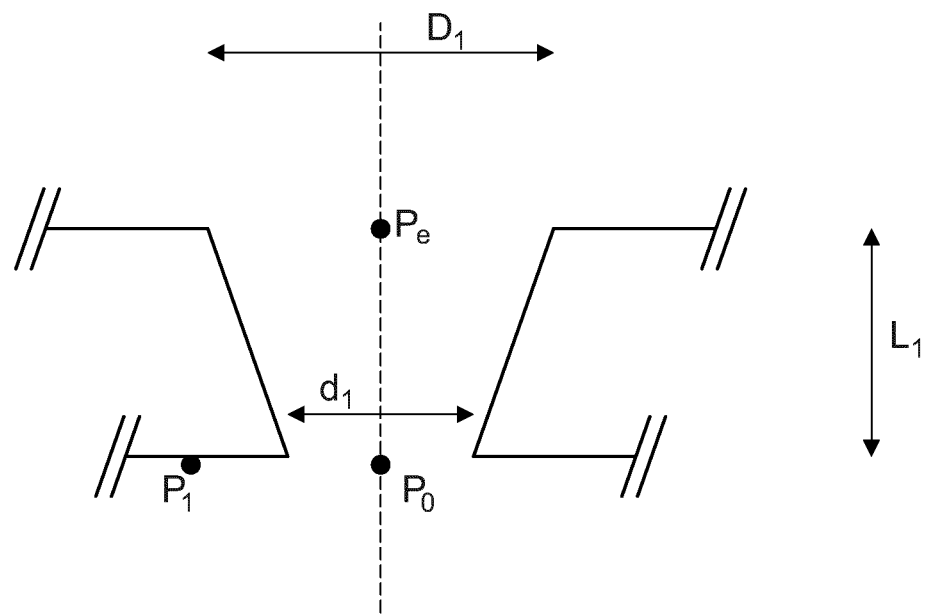
FIG. 1 depicts the geometrical properties of one embodiment of a collimator.

While the disclosure has been illustrated and described in detail in the drawings and foregoing description, such illustration and description are to be considered illustrative or exemplary and non-restrictive; the disclosure is thus not limited to the disclosed embodiments. Variations to the disclosed embodiments can be understood and effected by those skilled in the art and practicing the claimed disclosure, from a study of the drawings, the disclosure, and the appended claims.

As used herein, including in the claims, singular forms of terms are to be construed as also including the plural form and vice versa, unless the context indicates otherwise. Thus, it should be noted that as used herein, the singular forms "a," "an," and "the" include plural references unless the context clearly dictates otherwise.

The mere fact that certain measures are recited in mutually different dependent claims does not indicate that a combination of these measures cannot be used to fulfill aspects of the present invention. The present technology is also understood to encompass the exact terms, features, numerical values or ranges etc., if in here a relative term, such as "about", "substantially", "ca.", "generally", "at least", "at the most" or "approximately" is used in this specification, such a term should also be construed to also include the exact term. That is, e.g., "substantially straight" should be construed to also include "(exactly) straight". In other words, "about 3" shall also comprise "3" or "substantially perpendicular" shall also comprise "perpendicular". Any reference numerals in the claims should not be considered as limiting the scope.

In the claims, the terms "comprises/comprising", "including", "having", and "contain" and their variations should be understood as meaning "including but not limited to", and are not intended to exclude other components. Furthermore, although individually listed, a plurality of means, elements or method steps may be implemented. Additionally, although individual features may be included in different claims, these may possibly advantageously be combined, and the inclusion in different claims does not imply that a combination of features is not feasible and/or advantageous. In addition, singular references do not exclude a plurality.

Whenever steps were recited in the above or also in the appended claims, it should be noted that the order in which the steps are recited in this text may be the preferred order, but it may not be mandatory to carry out the steps in the recited order. That is, unless otherwise specified or unless clear to the skilled person, the order in which steps are recited may not be mandatory. That is, when the present document states, e.g., that a method comprises steps (A) and (B), this does not necessarily mean that step (A) precedes step (B), but it is also possible that step (A) is performed (at least partly) simultaneously with step (B) or that step (B) precedes step (A). Furthermore, when a step (X) is said to precede another step (Z), this does not imply that there is no step between steps (X) and (Z). That is, step (X) preceding step (Z) encompasses the situation that step (X) is performed directly before step (Z), but also the situation that (X) is performed before one or more steps (Y1), . . . , followed by step (Z). Corresponding considerations apply when terms like "after" or "before" are used.

It will be appreciated that variations to the foregoing embodiments of the invention can be made while still falling within the scope of the invention can be made while still falling within scope of the invention. Features disclosed in the specification, unless stated otherwise, can be replaced by alternative features serving the same, equivalent or similar purpose. Thus, unless stated otherwise, each feature disclosed represents one example of a generic series of equivalent or similar features.

Use of exemplary language, such as "for instance", "such as", "for example" and the like, is merely intended to better illustrate the invention and does not indicate a limitation on the scope of the invention unless so claimed. Any steps described in the specification may be performed in any order or simultaneously, unless the context clearly indicates otherwise. All of the features and/or steps disclosed in the specification can be combined in any combination, except for combinations where at least some of the features and/or steps are mutually exclusive. In particular, preferred features of the invention are applicable to all aspects of the invention and may be used in any combination.

Reference numbers and letters appearing between parentheses in the claims, identifying features described in the embodiments and illustrated in the accompanying drawings, are provided as an aid to the reader as an exemplification of the matter claimed. The inclusion of such reference numbers and letters is not to be interpreted as placing any limitations on the scope of the claims.

DESCRIPTION OF THE FIGURES

FIG. 1 depicts a single layer of material that is adapted to absorb radiation doses of an electron beam source that emits near parallel pathways of electrons. $D_1$ represents the area of a recess integrated in the first side of the absorbing material. The recess may have various shapes or geometries; one shape of the recess may substantially show up as a truncated cone. However, any shape may be advisable, such as a truncated pyramid with a random number of corners, regularly or irregularly. The dimension $d_1$ represents the area of the recess at the exit (or second) side of the absorbing material. The dashed line between $P_e$ and $P_0$ with its extensions represents an imaginary axis that may be considered to be the center of area of $D_1$ and/or $d_1$. $P_e$ is the reference point of entry of the electron beam, the point where the intensity of the emitted electron beam is defined as the reference value for further comparisons. $P_0$ shall represent the point of exit of the electron beam at the second side of the absorbing layer. $P_1$ represents any point on the second side of the absorbing material, representing the region of interest for the radiation sensitive part of the device to be irradiated.

In other words, a single layer of absorbing material with a truncated conical hole (recess) is displayed. $D_1$ represents the size of the beam facing contour of the recess, $d_1$ represents the size of the beam exit side contour of the recess, $L_1$ represents the thickness of the absorber material layer. $P_e$ represents a reference point at which the entrance dose is determined, $P_0$ represents the maximum exit dose location and $P_1$ represents the control point at which the maximum tolerable dose shall be achieved.

Figure 2:
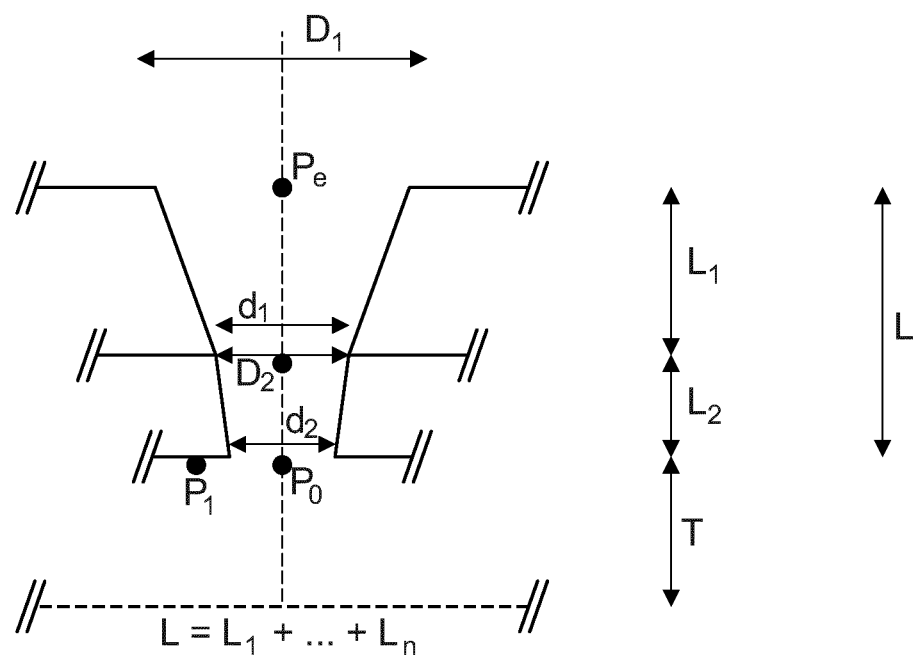
FIG. 2 depicts an alternate embodiment with a plurality of layers.

FIG. 2 represents an embodiment of the absorbing material with a collimator. The absorbing material may comprise more than one layer. One purpose to supply a further layer may be to reduce X-rays being emitted from particles of the layer with the thickness $L_1$ once they have been hit by an electron. The total thickness of the absorbing material may be formed by the sum of the thicknesses of the various layers. $L_2$ shall represent the thickness of a second layer; however, even more than two layers may be advisable to receive individual results. Such, a first layer may be optimized to reduce the dose of the electron beam, while the second layer may be optimized to reduce X-rays further. Further layers ($L_2 \ldots L_n$) may be applied to receive further properties depending on the application. The recess acting as a collimator can have different shapes in the distinct layers. As explained in FIG. 1, $D_1$ is the area of the collimator opening to a recess on the first side of the absorber material and may comprise different shapes; one shape may be circular to form the larger diameter of a truncated cone. However, other shapes may be comprised like an n-edged truncated pyramid, regularly or irregularly. The distant side (or the second side) of the first absorber has an area of $d_1$ that is substantially smaller than area $D_1$. However, although area $d_2$ in this representation is displayed as being smaller than area $d_1$, it may anyhow have the same size as $d_1$ or even be larger. The area at $d_2$ may be considered similar to $d_1$ in this embodiment.

$P_e$ is, as described in FIG. 1, the reference point at the side of the collimator that is closer to the source of the electron beam, P0 remains the reference point at the exit of the collimator as a whole. This relation remains constant no matter how many layers if absorber materials are applied. Reference points $P_0$ and also $P_1$ are always understood to be located on the second side of the absorber, the second side being the exit side of the electron beam after is has passed through the collimator.

To put this in short words, a plurality of layers of materials with the same reference dimensions and dose points is shown. $P_0$ and $P_1$ are always chosen at the exit side of the last layer. The total thickness of the absorber is the sum of the thicknesses of the individual layers ($L=L_1+ \ldots +L_n$).

Figure 3:
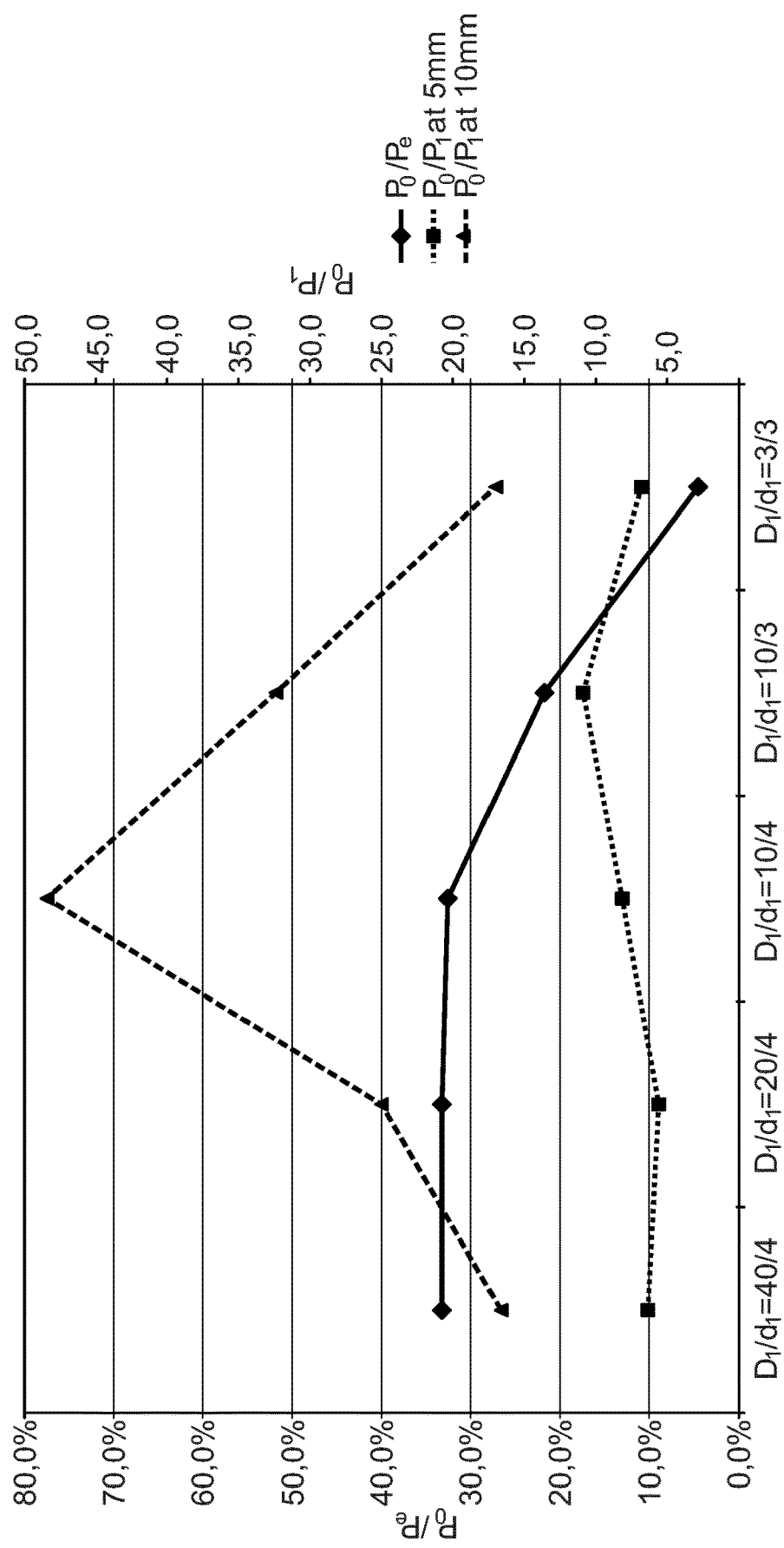
FIG. 3 depicts a graphical representation of determined values.

FIG. 3 shows 3 curves. The rhombic measuring points (standing on a tip) that form the steady line indicate the ratio of beam intensities in a percent value (left scale). For instance, the left most rhomb shows that at a ratio of conical diameters between the first side of the absorbing material (i.e. $P_e$, see FIG. 1 or 2) to the second side of the collimator at $P_0$ (see FIGS. 1 and 2) of $D_1/d_1$ is 40/4. At this ratio of diameters an output of 34% of the intensity of the electron beam at $P_e$ (the entrance point of the beam) can be detected at $P_0$. This intensity remains approximately constant over the ration $D_1/d_1$ of 20/4 till the point $D_1/d_1=10/4$. The values reduce to 22% at $D_1/d_1=10/3$ and nearly vanish if the conical recess comprises a near cylindric shape ($D_1/d_1=3/3$).

Surprisingly, the value of collimated electron beam ratio ($P_0/P_e$) remains nearly constant for a diameter ration of $D_1/d_1=40/4$ up to a reduction of $D_1$ to a ratio $D_1/d_1$ of 10/4. Only if the secondary side of the diameter is further reduced, the ration decreases significantly as can be seen from the curve.

In the following and throughout the whole document, the abbreviation DR (dose ratio) and DFR (dose factor ratio) are meant to be interchangeable, they reference the same phenomenon.

The dotted line that connects the quadratic points represents that the reduction rate (DFR=dose factor ratio) is as low values between 5 and around 10, if the distance between $P_0$ and $P_1$ is around 5 mm. Thus, the DFR at point $P_0$ related to the dose at point $P_1$ is between 5 and 10 at a 5 mm distance between the points $P_0$ to $P_1$.

Again, surprisingly, if a distance between the points $P_0$ and $P_1$ is increased to 10 mm, the resulting curve, represented by triangles and connected with a dashed line, show an entirely different behavior. At a ratio of the diameters of $D_1$ to $d_1$ of 10/4, a sudden high reduction of the ratio $P_0/P_1$ can be observed. A reduction of nearly a ratio of 50 ($P_0/P_1$) means that the shape and dimension of the cone that forms the collimator at $P_1$ is observed related to $P_0$. Thus, the radiation beam at $P_0$ is nearly 50 times stronger than at $P_1$ (that is 10 mm away from $P_0$ in either (planar) direction, as long as the second side of the absorber is observed).

Thus, the trends with changing $D_1/d_1$ values at constant L $P_0/P_1$ and $P_0/P_e$ and are reached with $D_1/d_1=10/4$.

Figure 4:
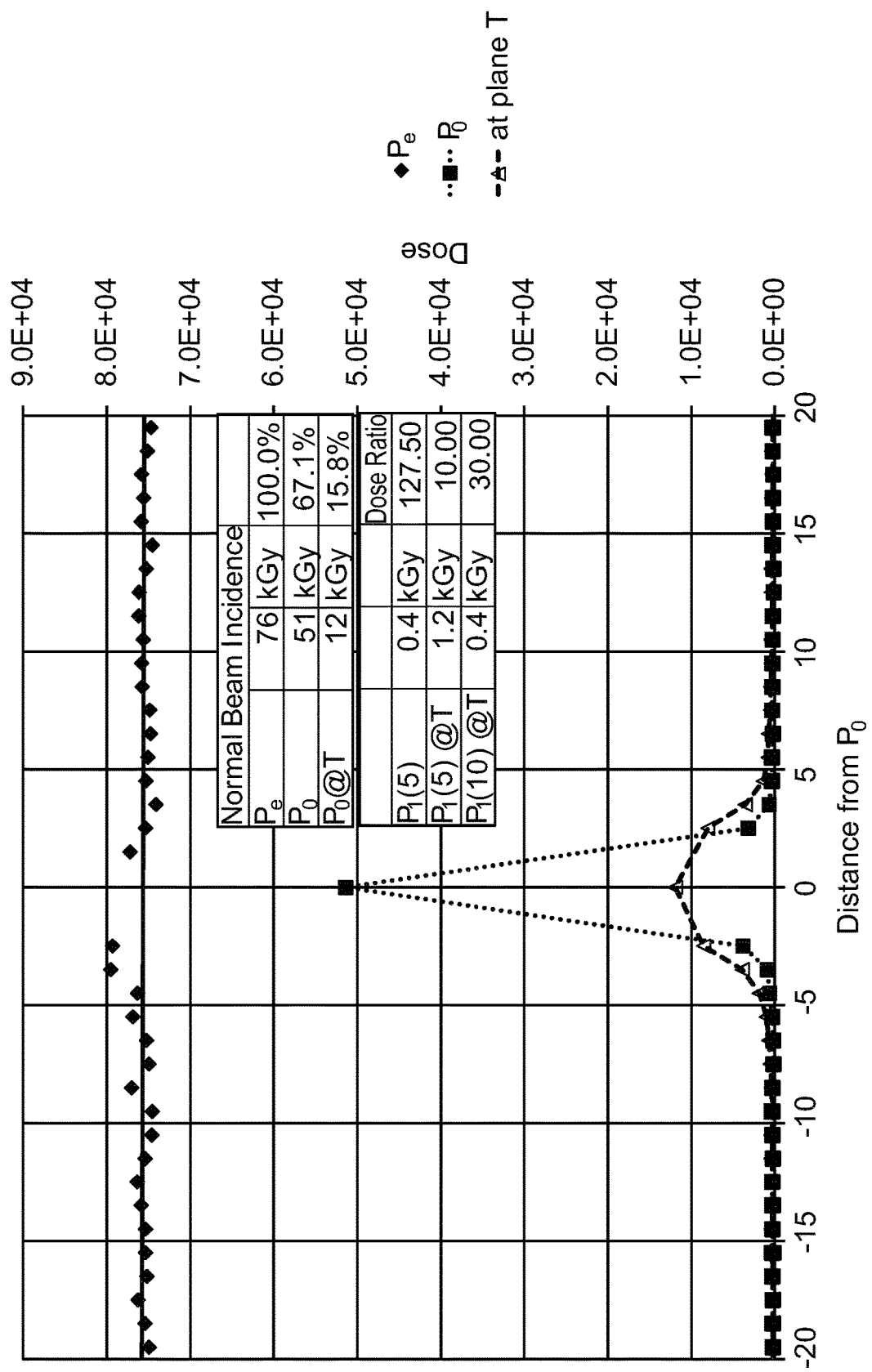
FIG. 4 depicts a graphical illustration of properties as achieved by a cylindrically shaped collimator

FIG. 4 depicts the situation provided a generally cylindric recess is selected, an embodiment that is used widely. While the (nearly) steady line with the rhombic points indicate a widely constant radiation beam at the first side, the transmission to P0 at the second side of the (cylindric) collimator reaches up to some 67% of the dose at the entrance point Pe. The center line at x=0 (of the coordinate system) represents the axis running through Pe and P0 (see FIGS. 1 and 2), thus, the axial center of the recess. Further, the x-axis in the coordinate system shows the reduction of the doses if point $P_1$ is moved away perpendicular to the virtual axis from $P_0$ (the exit point of the collimator). The further $P_1$ is distant from $P_0$ the less dose is received of the dose becomes; this could be expected. When point $P_0$ and the corresponding points $P_1$ are shifted in a certain distance from the surface of the second side of the absorber, thus forming a parallel flat area in distance T from the surface of the second side of the absorber (see FIG. 3), the dose distribution broadens and flattens; the peak value is reduced substantially.

In this example representation, an input dose of 76 kGy at $P_e$ results in a reduced Dose of 67% at $P_0$. If $P_0$ is relocated to a distant (parallel) plane with the distance T to the surface of the second side of the absorber, the Dose is reduced to nearly 16% of the value at $P_e$.

The goal is to optimize 2 parameters: 1) the transmission $P_0/P_e$ and 2) the dose ratio at the protected location ($P_0/P_1$).

Figure 5:
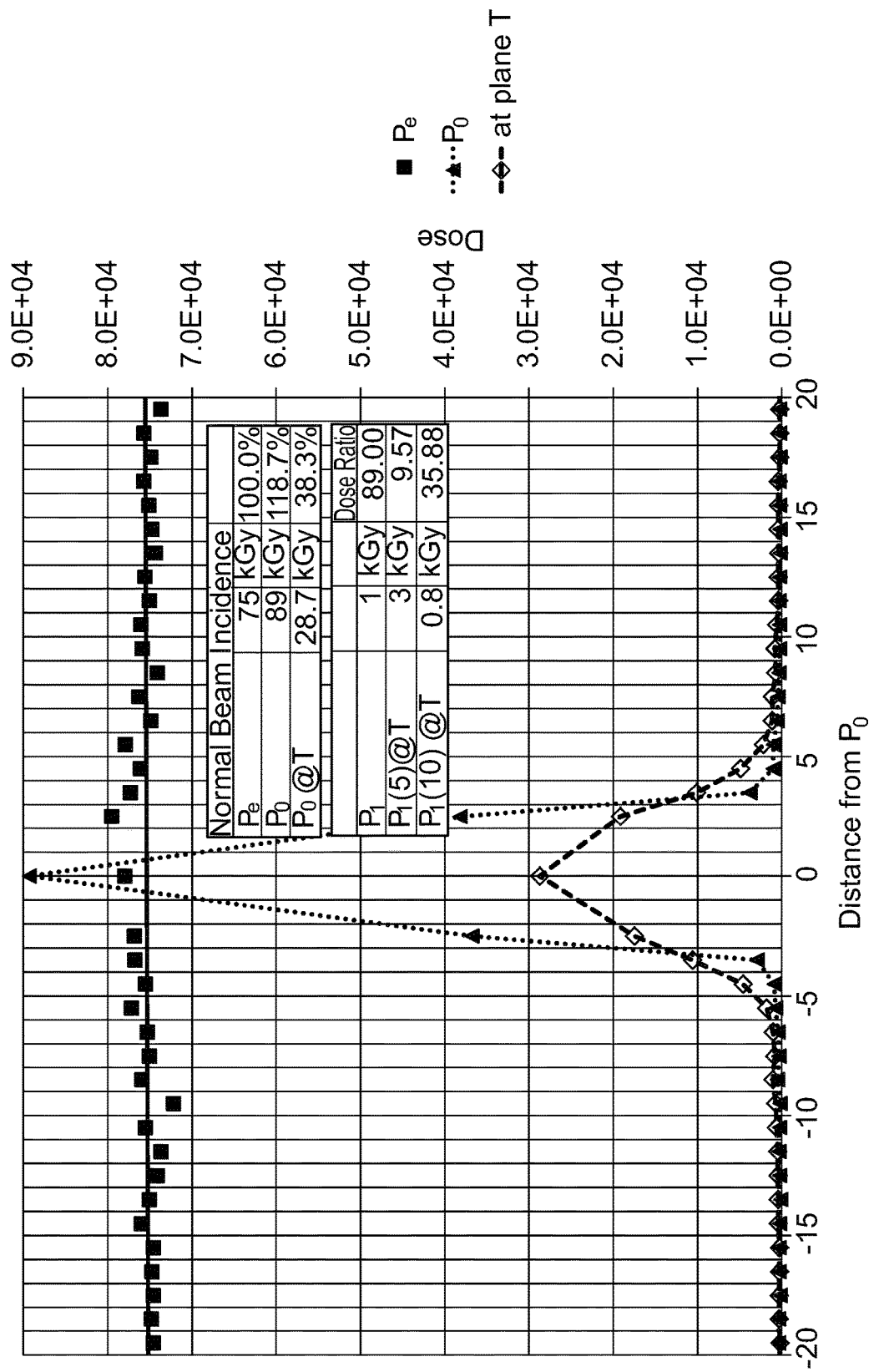
FIG. 5 depicts the difference of a conical collimator compared to the embodiment in FIG. 4.

FIG. 5 depicts the dose distribution if a conical recess is integrated into the first absorber material followed by a cylindrical recess with 4 mm diameter in a second absorber. Here, a bore relation of 10/4 is selected; i.e., the ratio of D1 to d1 is 10/4 (see FIGS. 1 and 2). Again, same as in FIG. 4, a steady source radiation dose of around 75 kGy is input into the system. An overshooting value has been determined, surprisingly, thus, a value on the secondary side of more than what was input. This may have statistical reasons; however, likely is also a concentration (or focusing) effect. The rays entering the collimator via $D_1$ may be reflected or concentrated to the diameter at $d_1$. At least, at the virtual axis running through $P_e$ and $P_0$ (see FIGS. 1 and 2) the resultant values on the secondary side are significantly higher compared to a configuration where the collimator recess has only a cylindric shape. The overshoot effect is quickly reduced when the Dose is analyzed further away from $P_0$, at the same distance T as used FIG. 4. However, transmission at T and dose ratio are much improved.

Figure 6:
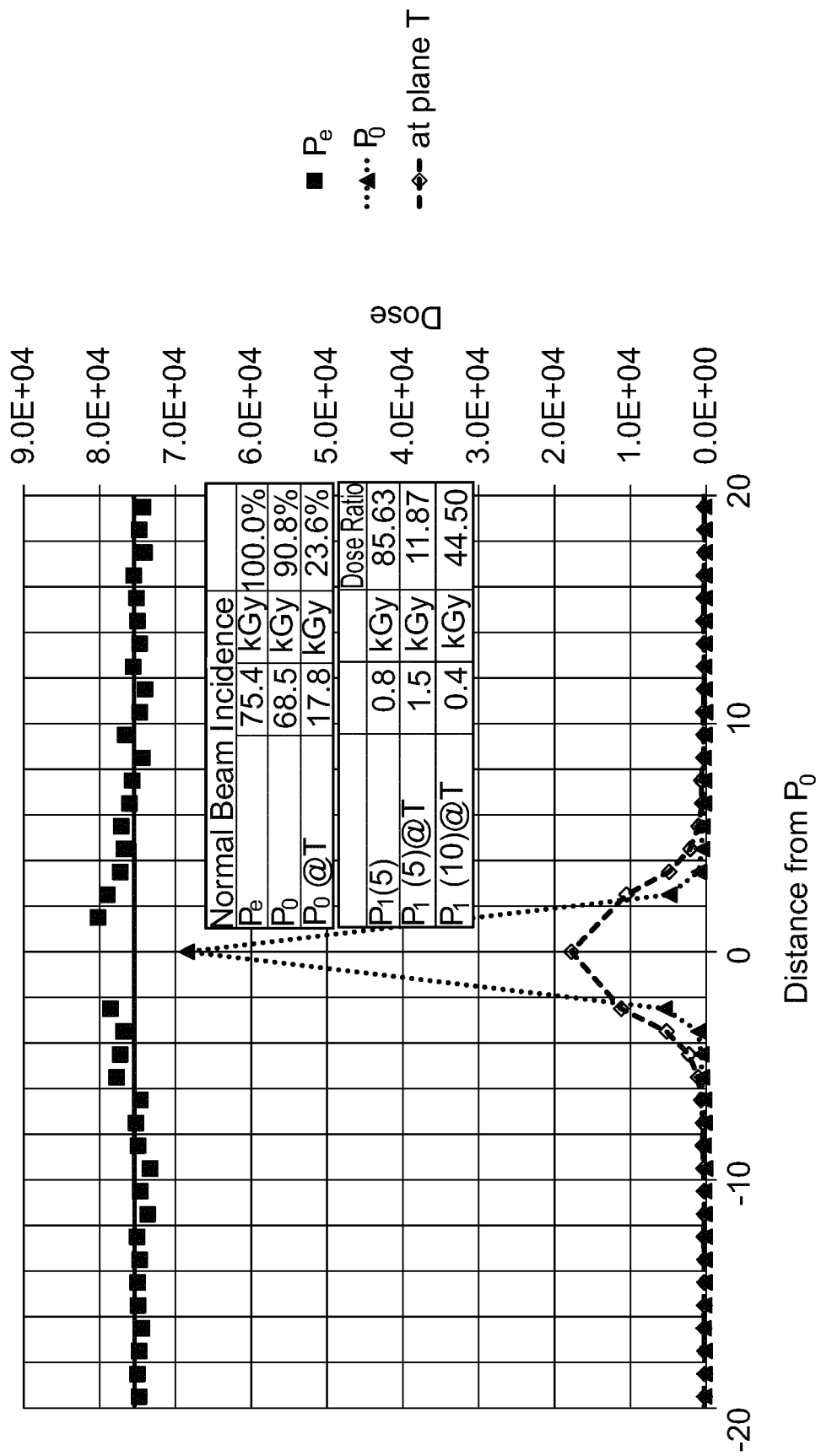
FIG. 6 depicts, as in FIG. 5, a conical collimator, however with different dimensions and properties.

FIG. 6 depicts the dose distribution if a conical recess is integrated into the first absorber material followed by a cylindrical recess with 3 mm diameter in a second absorber. Here, a bore relation of 10/3 is selected; i.e., the ratio of $D_1$ to $d_1$ is 10/3 (see FIGS. 1 and 2). Again, same as in FIG. 4, a steady source radiation dose of around 75 kGy is input into the system. A transmission value $P_0/P_e=90\%$ has been determined, thus, a value on the secondary side of nearly what was input. At the virtual axis running through Pe and $P_0$ (see FIGS. 1 and 2) the resultant values on the secondary side are significantly higher compared to a configuration where the collimator recess has a cylindric shape. At the distances at $t_2$ and $t_4$ reduced values follow, however, both of them show roughly a bell curve, only slightly improved from FIG. 4.

The invention claimed is:

1. A collimator system to control and/or collimate radiation originating from an electron beam source for sterilization of a medical product, comprising:
    a collimator having a thickness L including:
    at least a first absorber comprising a first side configured to allow electron beam entry and a second side opposite to the first side,
    a first recess opening at the first side having a diameter of dimension $D_1$ and a second recess opening at the second side having a diameter of dimension $d_1$;
    wherein dimension $D_1$ is larger than dimension $d_1$, and
    wherein $D_1$ and $d_1$ are configured such that an electron dose $P_0$ measured at the second recess opening is at least 20% of an electron dose $P_e$ measured at the first recess opening and such that an electron dose $P_1$ measured at a location on the second side spaced a distance away from the second recess opening is at most 20% of the electron dose $P_0$ at a constant collimator thickness L; and
    wherein the medical product comprises an integrated circuit and a sensor configured for subcutaneous use, wherein the medical product is arranged with the collimator such that the sensor is positioned beneath the second recess and the integrated circuit is positioned beneath the location on the second side.

2. The collimator system according to claim 1 wherein a ratio $D_1/d_1$ is at least 1.25, and at most 5.

3. The collimator system according to claim 1 wherein the first absorber has more than one layer that are made of different materials.

4. The collimator system according to claim 1 wherein at least a second absorber is provided behind or downstream with respect to the second side.

5. The collimator system according to claim 4 wherein the second absorber is attached to and/or integrated into the first absorber and has an annular shape.

6. The collimator system according to claim 4 wherein the second absorber is separate from the first absorber and is configured to protect and/or encapsulate an element of the medical product.

7. The collimator system according to claim 6, wherein the element includes an integrated circuit of a product to be sterilized.

8. The collimator system according to claim 4 wherein the at least second absorber comprises a material with a higher average atomic number than the first absorber and comprises at least one of
    a polymer;
    an electrically conducting polymer;
    a polymer comprising metal particles;
    a polymer comprising at least one metal piece;
    a semiconductor; and
    a metal.

9. The collimator system according to claim 4 wherein the first absorber comprises at least two layers, wherein a thickness of the first layer $L_1$ is selected based on a range of electrons beams at the selected electron beam energy in the same material without recess, and wherein a thickness of the successive layers $L_2+L_N$ is configured for absorption of scattered electrons and x-rays generated by electron interaction with all materials.

10. The collimator system according to claim 4 wherein the first absorber and second absorber are configured so that a dose ratios $P_0/P_e$ and/or $P_0/P_1$ are simultaneously configured at a constant thickness L, whereby $D_1$ and $d_1$ are configured to enhance radiation dose contributions to $P_0$ and $P_1$.

11. The collimator system to claim 4 wherein the first absorber and second absorber have more than one layer and at each layer the diameter at the more open side is $D_X$ and at the more closed side is $d_x$ and the ratio(s) of $D_x/d_x$ are configured to enhance remaining electron scatter and x-ray dose contributions to $P_0$ and $P_1$ wherein $P_0$ is the dose at the second side of the absorber in the region of the recess and $P_1$ is the dose at the second side of the absorber away from the region of the recess.

12. The collimator system of claim 1, wherein the collimator and the medical product are attached and/or assembled to each other.

13. The collimator system according to claim 1, wherein $D_1$ is within a range of 3 mm to 20 mm.

14. The collimator system according to claim 1, wherein $d_1$ is within a range of 1 mm to 10 mm.

15. The collimator system according to claim 1, wherein a ratio $D_1/d_1$ is at least 2.5, and at most to 10.

16. Method to control and/or focus radiation originating from an electron beam source, comprising:
    providing at least a first collimator system according to claim 1;
    irradiating the medical product with electrons from the electron beam source.

17. The method according to claim 16, further comprising conveying the medical product continuously, and simultaneously irradiating it from top and/or bottom and/or from one or both sides.

* * * * *